United States Patent
Yoon

(10) Patent No.: US 7,232,661 B2
(45) Date of Patent: Jun. 19, 2007

(54) DIAGNOSTIC AGENTS FOR THE PRENATAL DIAGNOSIS OF PRETERM DELIVERY, FETAL INFECTION, AND FETAL DAMAGE, AND DIAGNOSTIC KIT CONTAINING THE SAME

(75) Inventor: Bo Hyun Yoon, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 0 days.

(21) Appl. No.: 10/415,763

(22) PCT Filed: Aug. 1, 2001

(86) PCT No.: PCT/KR01/01306

§ 371 (c)(1), (2), (4) Date: Apr. 30, 2003

(87) PCT Pub. No.: WO02/42770

PCT Pub. Date: May 30, 2002

(65) Prior Publication Data

US 2004/0029176 A1  Feb. 12, 2004

(30) Foreign Application Priority Data

Nov. 21, 2000 (KR) ...................... 10-2000-0069283

(51) Int. Cl.
- G01N 33/53 (2006.01)
- G01N 33/543 (2006.01)
- G01N 33/545 (2006.01)
- G01N 33/548 (2006.01)
- G01N 33/552 (2006.01)
- G01N 33/573 (2006.01)
- G01N 33/577 (2006.01)
- C07K 16/40 (2006.01)

(52) U.S. Cl. ...................... 435/7.94; 435/7.1; 435/7.4; 435/7.92; 435/23; 435/287.2; 435/288.3; 436/510; 436/518; 436/527; 436/528; 436/530; 436/531; 436/172; 530/388.26; 530/389.1

(58) Field of Classification Search ................ 435/7.1, 435/7.4, 7.92, 7.94, 23, 174, 176, 180, 287.2, 435/288.3, 806, 975; 436/501, 510, 518, 436/527, 528, 531, 164, 172, 807–809, 815, 436/906, 530; 600/551; 530/388.26, 389.1
See application file for complete search history.

(56) References Cited

U.S. PATENT DOCUMENTS 5,545,616 A  8/1996  Woodruff et al.
5,597,700 A  1/1997  Konstantinov et al.
5,736,341 A *  4/1998  Sorsa et al. .................. 435/7.1

OTHER PUBLICATIONS

Maymon et al., Jul. 2000. Human neutrophil collagenase (matrix metalloproteinase 8) in parturition, premature rupture of membranes, and intrauterine infection. Am. J. Obstet. Gynecol. 183 (1): 94-99.*

Matsuki et al., 1996. A one-step sandwich enzyme immunoassay for human matrix metalloproteinase 8 (neutrophil collagenase) using monoclonal antibodies. Clinica Chimica Acta 244: 129-143.*

Amersham Biosciences, 2002. Matrix metalloprotienase-8 (MMP-8, neutrophil collagenase), human, BIOTRAK ELISA system. Instructions. Product code RPN2619. Amersham Biosciences UK Limited.*

Yoon et al., Jan. 2001. Amniotic fluid matrix metalloproteinase-8: an index of funisitis and the fetal inflammatory response syndrome. Am J. Obstet. Gynecol. 184 (1): pS31. Abstract No. 0066.*

Maymon et al., Jan. 2001. The diagnostic and prognostic value of MMP-8 in the evaluation of preterm labor. Am. J. Obstet. Gynecol. 184 (1): pS31. Abstract No. 0068.*

Yoon et al., Jan. 2001. An elevated amniotic fluid matrix metalloproteinase-8 at the time of midtrimester genetic amniocentesis identifies patients at risk for spontaneous preterm delivery. Am J. Obstet.Gynecol. 184 (1): pS7. Abstract No. 0014.*

Morrison et al., *Eur. J. Obstet. Gynecol. Reprod. Biol.*, 54: 71-75 (1994).

Tu et al., *Obstet. & Gynecol.*,92(3): 446-449 (1998).

Watari et al., *Am. J. Pathol.*,154(6): 1755-1762 (1999).

Vadillo-Ortega et al., *Obstet. & Gynecol.*,75(1): 84-88 (1990).

Okada et al., *J Biol. Chem.*, 267(30) 21712-21719 (1992).

* cited by examiner

*Primary Examiner*—Long V. Le
*Assistant Examiner*—James L. Grun
(74) *Attorney, Agent, or Firm*—JHK Law; Joseph Hyosuk Kim

(57) ABSTRACT

This invention is about a method for the prenatal diagnosis of preterm delivery, fetal infection, and fetal damage, and diagnostic reagent system and diagnostic kit for the diagnosis. The method, diagnostic reagent system, and kit are based on the finding that the level of MMP-8 in the amniotic fluid is significantly higher when the pregnant woman is at risk for preterm delivery, intrauterine infection, and fetal damage. The diagnostic reagent system and kit can be applied to patients with or without clinical signs of preterm labor or premature rupture of fetal membranes. With its superiority in sensitivity and specificity as well as its less invasiveness compared to the conventional method of measuring fetal blood cytokine levels, this diagnostic reagent system and kit is very useful in the prenatal diagnosis of preterm delivery, fetal infection, and fetal damage.

8 Claims, 6 Drawing Sheets

DIAGNOSTIC AGENTS FOR THE PRENATAL DIAGNOSIS OF PRETERM DELIVERY, FETAL INFECTION, AND FETAL DAMAGE, AND DIAGNOSTIC KIT CONTAINING THE SAME

FIELD OF THE INVENTION

The present invention relates to a diagnostic reagent system for the prenatal diagnosis of preterm delivery, fetal infection, and fetal damage, and a diagnostic kit using the same reagents and, more particularly, to the use of an amniotic fluid matrix metalloproteinase-8 (MMP-8) concentration as a prenatal diagnostic marker for preterm delivery, fetal infection, and fetal damage.

BACKGROUND OF THE INVENTION

It has long been recognized in the medical world that the prevention of preterm delivery or premature rupture of fetal membranes is preferred to the post-treatment thereof. However, a great variety of factors are now known to cause preterm delivery or premature rupture of fetal membranes, making it difficult to prevent these undesirable events. The traditional approach to the prevention of preterm delivery has been identifying a high-risk group of women to which special attention should be paid based on the knowledge of obstetrics and gynecology, demography, and various syndromes (Main et al., Am. J. Obstet. Gynecol., 151:892-898, 1985). However, this approach has the problem of being neither sensitive nor specific. To circumvent this problem, extensive research has been directed to finding biochemical markers for the prediction of impending preterm delivery and premature rupture of fetal membranes, resulting in the nomination of plasma estradiol-17 beta, progesterone, C-reactive protein as promising candidates. However, these candidates were found to be of poor accuracy.

Besides the identification of such biochemical predictable markers, significant attention has been paid to the biochemical role of collagen, based on the fact that the chorionic membrane is composed of fibrous connective tissue and the tensile strength of fibrous connective tissue is determined by its collagen content, as revealed through studies of the premature rupture of fetal membranes. On the basis of their findings that prematurely ruptured fetal membranes have low collagen content compared to normal membranes, some scientists concluded that the premature rupture of fetal membranes is attributable to their low tensile strength compared to that of normal fetal membranes (Obstet. Gynecol., 57:487-89, 1981). According to another study, it has been reported that the serum activity of collagenase was high in prematurely ruptured fetal membranes and preterm labor (Obstet. Gynecol., 75:84-88, 1990). However, the precise mechanism of such biochemical changes has not yet been elucidated (FEBBS Letters, 244(2):315-318, 1989).

Statistically, the frequency of preterm delivery before 37 weeks of gestation is estimated to be about 8 to 10%. In Korea, about 50,000 neonates are prematurely delivered every year. Preterm delivery often causes serious neonatal complications including sepsis, respiratory distress syndrome, pneumonia, bronchopulmonary dysplasia, intraventricular hemorrhage, necrotizing enterocolitis and cerebral palsy. The frequency and severity of such sequelae is greater the earlier the preterm delivery. Therefore, if preterm delivery is prevented, it will be possible to remarkably reduce the occurrence of premature neonates disabled by such diseases.

Recent reports disclose that at least 30 to 40% of preterm deliveries are associated with intrauterine infection (Butler N R., Bonham D G., Prenatal mortality. The first report of the British perinatal mortality survey, Edinburgh, Churchill Livingstone, 115-145, 1963; Romero R., Avila C., Sepulveda W., Preterm birth. Cause, prevention, and management., McGrow-Hill Company, 97-136, 1993; Romero R., Mazor M., Clin. Obstet. Gynecol., 31:553, 1990; Gibbs R S., Romero R., Hiller S L., et al., Am. J. Obstet. Gynecol., 166:1515, 1992).

Intrauterine infection may cause fetal damage by the following process. Intrauterine infection activates the maternal and fetal immune system to secrete inflammatory mediators, such as cytokines from lymphocytes and MMPs (matrix-metalloproteinases) from neutrophils. When the inflammatory mediators reach a certain level, prostaglandin, which promotes uterine contraction, is produced causing active labor leading to preterm delivery. Additionally, increased levels of inflammatory mediators cause the fetus to be affected by fetal inflammatory response syndrome (FIRS). Inflammatory mediators cause sepsis or acute respiratory distress syndrome or damage organs as a result of autoimmune diseases in adults. Likewise, fetal organs can be systemically injured by inflammatory mediators, resulting in brain white matter lesions and bronchopulmonary dysplasia. Therefore, the prenatal diagnosis of intrauterine inflammation is essential for the prevention of preterm delivery and fetal damage.

Generally, the prenatal diagnostic methods of intrauterine fetal infection in current use are cordocentesis, in which fetal blood cytokine levels are measured, and histologic examination of the umbilical cord to identify funisitis. However, cordocentesis is limited in its usage due to its invasiveness, and funisitis can be diagnosed only after delivery (Yoon B H., Romero R., Park J S., Kim C J., Choi J H., Han T R., Am. J. Obstet. Gynecol., 182:675-81, 2000; Yoon B H., Romero R., Kim K S., Park J S., Ki S H., Kim B I., Jun J K., Am. J. Obstet. Gynecol., 181:773-9, 1999; Romero R., Gomez R., Ghezzi F., Yoon B H., Mazor M., Edwin S S., Berry S M., Am. J. Obstet. Gynecol., 179:186-93, 1998).

The white blood cell count in the amniotic fluid is increased in cases of infection or inflammation of the amniotic cavity. Neutrophils in the amniotic fluid are considered to be of fetal origin (Knauper V., Kramer S., Reinke H., Tschesche H., Eur. J. Biochem., 189:295-300, 1990; Blaser J., Triebel S., Massjosthusmann U., Romisch J., Krahl-Mateblowski U., Freudenberg W., Fricke R., Tschesche H., Clinic. Chim. Acta., 244:17-33, 1996; Segura-Valdez L., Pardo A., Gaxiola M., Uhal B D., Becerril C., Selman M., Chest., 117:684-94, 2000; Romanelli R., Mancini S., Laschinger C., Overall C M., Sodex J., MaCulloch C A., Infect. Immun., 67:2319-26, 1999; Maymon E., Romero R., Pacora P., Gomez R., Athayde N., Edwin S., Yoon B H., Am. J. Obstet. Gynecol., 183:94-9, 2000). Therefore, it is postulated that secretory products of neutrophils in amniotic fluid might reflect a fetal inflammatory response. The focus of the present invention is the level of MMP-8 in the amniotic fluid. The determination of MMP-8 in amniotic fluid may be a marker of the fetal inflammatory response syndrome which can be diagnosed currently by histologic examination of the umbilical cord after delivery or by cordocentesis with the determination of fetal blood cytokines.

MMP (matrix metalloproteinase) series, also collectively known as matrixins, are zinc-dependent endopeptidases that function to degrade extracellular matrix proteins. These proteases constitute a large and growing family of proteins which share similar structures and enzymatic properties. MMPs are broadly classified into five groups. Along with MMP-1 and MMP-13, MMP-8 belongs to an interstitial collagenase group. MMP-8 is similar in size to other interstitial collagenases but is glycosylated to a far greater extent. A fully glycosylated proenzyme form of MMP-8 has a molecular weight of 85 kDa. The proenzyme is converted into an active form of 60-70 kDa with the loss of a 15-25 kDa segment. ProMMP-8 is activated in vitro by various proteinases, including trypsin, chymotrypsin and cathepsin G. Organomercurial compounds were also found to activate proMMP-8. The activation mechanism of MMP-8 in vivo has not yet been fully clarified.

The prior technique concerning MMP-8 is found in U.S. Pat. No. 5,736,341, which discloses methods and test kits capable of sensitive and specific diagnosis of periodontal diseases based on monoclonal antibodies against MMP-8. The patent describes that since MMP-8 is directly associated with the destruction of periodontal connective tissues during the progression of periodontitis and diffused into the oral cavity through the gingival pocket containing gingival crevicular fluid, measurement of the MMP-8 level in the oral cavity enables the site-specific diagnosis of periodontitis. For the specific and sensitive biochemical detection of periodontal diseases in progression, these methods measure the conversion of a proform of MMP-8 into an active form because the conversion takes place during the process of periodontal infection. Nothing is mentioned about the use of MMP-8 in connection with preterm delivery and fetal infection and damage.

U.S. Pat. No. 5,641,636 refers to a method of predicting the onset of fetal membrane rupture based on the activity of another matrix collagenase, MMP-9, which belongs to a different group of enzymes from that of MMP-8. MMP-9 is a 92-kDa type IV collagenase/gelatinase or gelatinase B with the largest molecular weight among MMPs. For activation, the proenzyme form of MMP-9, i.e. proMMP-9, is initially cleaved into an intermediate active form of about 83 kDa with concurrent production of a 9 kDa inactive cleavage fragment. The intermediate active form is further processed proteolytically into an active form of MMP-9 with 67 kDa (J. Biol. Chem., 267 (30):21712-21719, 1992). The activation of MMP-9 means the conversion into the 83 kDa intermediate active form or the 67 kDa fully active form with gelatin degradation activity. This patent measures the hydrolytic activity of MMP-9 in degrading denatured collagens, e.g. gelatins, to diagnose the premature rupture of fetal membranes. However, because MMP-9 is already present in the amniotic fluid before the onset of parturition, this method has limited value in predicting the premature rupture of fetal membranes.

Approximately 30 to 40% of patients with preterm labor or premature rupture of fetal membranes undergo preterm delivery. In this condition, various substances, including interleukin-6, interleukin-8, TNF-α, interleukin-1β, GROα, RANTES, white blood cells, MIP-1α, MCP-1, glucose, $PGE_2$, and angiogenin, are known to be present at increased levels in the amniotic fluid. However, these substances are of poor utility for the prediction of preterm delivery because their levels remain unchanged or are not detected in the amniotic fluid of pregnant women without clinical signs of preterm labor and are increased only after the onset of preterm labor or premature fetal membrane rupture.

SUMMARY OF THE INVENTION

The intensive and thorough research on the prediction of preterm delivery, fetal infection, and fetal damage was conducted by the present inventors to overcome the problem of invasiveness of cordocentesis with the determination of fetal blood cytokines and the problem of post-delivery identification of funisitis through histologic examination of the umbilical cord. This resulted in the finding that the activity of MMP-8 is detected in the amniotic fluid of women without clinical signs of preterm labor or preterm premature rupture of fetal membranes as well as those with such signs, which allowed the development of a method and kit capable of diagnosing preterm delivery, fetal infection, and fetal damage.

Therefore, it is the objective of the present invention to provide a method and kit for the prenatal diagnosis of preterm delivery, fetal infection, and fetal damage in pregnant women with or without clinical signs of preterm labor or premature rupture of fetal membranes, whereby neonatal morbidity and serious complications or sequelae, such as cerebral palsy, can be prevented.

As one element of the present invention, a method is provided for the prenatal diagnosis of preterm delivery, fetal infection, and fetal damage, by measuring the level of MMP-8 in the amniotic fluid in pregnant women with or without clinical signs of preterm labor or premature rupture of fetal membranes.

As another element of the present invention, a diagnostic reagent system and kit for the prenatal diagnosis of preterm delivery, fetal infection, and fetal damage is provided.

DETAILED DESCRIPTION OF THE INVENTION

In one embodiment, the present invention pertains to determination of the activity of MMP-8 in the amniotic fluid, thereby prenatally diagnosing preterm delivery, fetal infection, and fetal damage.

With activity to degrade extracellular matrix proteins, MMP-8 is a zinc-dependent endopeptidase. Belonging to an interstitial collagenase group, MMP-8 can be purified from neutrophilic leukocytes in proenzyme form (proMMP-8). ProMMP-8 is highly glycosylated with a molecular weight of approximately 85 kDa. Activation of the proenzyme is achieved by cleavage of the proenzyme molecule, which creates the active collagenase whose molecular weight varies from 60 to 70 kDa, depending on the mode of activation. The mechanism of activation in vivo likely involves reactive oxygen species and oxidants such as hydroxyl radicals. When the N-terminal segment of the procollagenase are removed, the active site of the enzyme is generated and exposed.

MMP-8 is produced as a proenzyme form (proMMP-8) by neutrophilic leukocytes. ProMMP-8 exists in granules for storage and is secreted in response to stimuli. Secreted proMMP-8 is activated at extracellular interstitium and degrades type I, II and III collagens with high specificity for type I collagen. This enzyme, known as an important mediator of inflammation-related tissue injury, is involved in the tissue injury caused by inflammatory diseases such as periodontitis, chronic obstructive pulmonary disease, rheumatoid arthritis, etc. Also, MMP-8 is known to be implicated in the progression of labor by causing the effacement and dilatation of the uterine cervix.

Based on the finding that an elevated mid-trimester amniotic fluid concentration of MMP-8 in women both with and without clinical signs of preterm labor or premature rupture of fetal membranes is highly indicative of preterm delivery, the present inventors developed a prenatal diagnostic method of preterm delivery, fetal infection, and fetal damage.

In accordance with an embodiment of the present invention, a method for the prenatal diagnosis of preterm delivery, fetal infection, and fetal damage is provided, comprising the steps of:

1) sampling amniotic fluid from a pregnant woman; and
2) quantitatively measuring MMP-8 in the amniotic fluid sample.

Women with clinical signs of preterm labor or premature rupture of fetal membranes as well as women without such clinical signs can be diagnosed for preterm delivery.

The sampling of an amniotic fluid can be achieved by transabdominal amniocentesis under ultrasonographic guidance or other sampling processes. For quantitative determination of MMP-8 levels in the amniotic fluid, any analytic method, if based on antigen-antibody coupling, can be used, and ELISA (enzyme-linked immunosorbent assay) is preferred.

Figure 1:
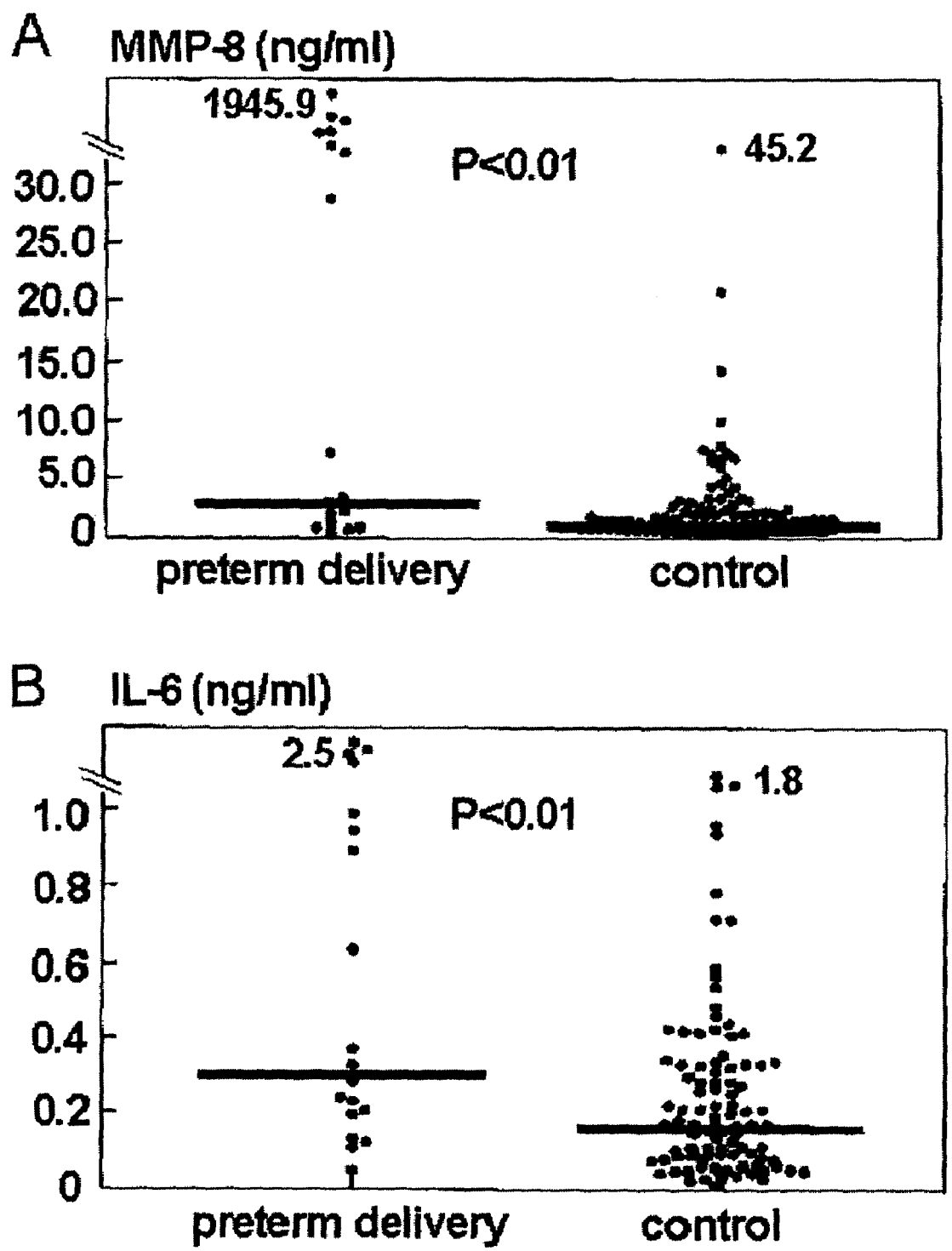
FIG. 1 shows distributions of amniotic fluid MMP-8 and IL-6 concentrations in patients with spontaneous preterm delivery and with spontaneous full-term delivery.

To determine if MMP-8 serves as a powerful clinical indicator for the prediction of preterm delivery in a mid-pregnancy stage, amniotic fluid concentrations of MMP-8 were compared with those of IL-6, another excellent indicator of inflammation, in patients who had a spontaneous preterm delivery before 32 weeks of gestation or a term delivery after mid-trimester amniocentesis without any clinical signs of impending preterm delivery. The amniotic fluid concentrations of MMP-8 and IL-6 were significantly higher in those with preterm delivery. Patient with an amniotic fluid MMP-8 concentration higher than 23 ng/ml had a spontaneous delivery in 89% of cases, as seen in FIG. 1. In addition, statistical comparison demonstrated the superiority of MMP-8 to IL-6 in sensitivity and specificity for the prediction of preterm delivery. Considering sensitivity, specificity and odds ratio as a whole, an amniotic fluid MMP-8 level of 23 ng/ml was selected as a cutoff suitable for the prediction of preterm delivery.

An elevated mid-trimester amniotic fluid MMP-8 concentration higher than the cutoff means high risk of preterm delivery before 32 weeks of gestation. Therefore, when genetic amniocentesis is conducted in a mid-pregnancy stage, the quantification of amniotic fluid MMP-8 levels is helpful in the identification of patients who are likely to undergo a preterm delivery.

To prove the usefulness of MMP-8 as a clinical predictor for fetal infection and fetal damage, amniotic fluids taken from consecutive patients who delivered preterm singleton neonates (gestational age <36 weeks) within 72 hours of amniocentesis were cultured for aerobic and anaerobic bacteria and for mycoplasmas and amniotic fluid MMP-8 concentrations were determined by ELISA. A histologic examination of placenta was made after delivery. MMP-8 concentrations were observed to be significantly higher in patients with a positive amniotic fluid culture than in patients with a negative amniotic fluid culture. Also, the presence of histologic chorioamnionitis in placenta entailed a significantly higher amniotic fluid MMP-8 level than the absence thereof (see data of Tables 1 to 4).

From these results, it can be inferred that the infection of amniotic fluid with microorganisms leads to such a significant increase in amniotic fluid MMP-8 level that quantification thereof can be diagnostic of intrauterine infection. As for histologic chorioamnionitis, it also induces a significant increase of amniotic fluid MMP-8 level, so that the determination of the amniotic fluid MMP-8 level can reflect the intrauterine infection. In consequence, MMP-8 can be used as an effective clinical predictor for the prenatal diagnosis of intrauterine infection and inflammation as well as preterm delivery. Especially, quantification of amniotic fluid MMP-8 levels can diagnose intrauterine inflammation with higher specificity and positive predictive value.

In order to diagnose fetal infection straightforwardly, amniotic fluid concentrations of MMP-8 were compared according to the presence or absence of funisitis.

Figure 3:
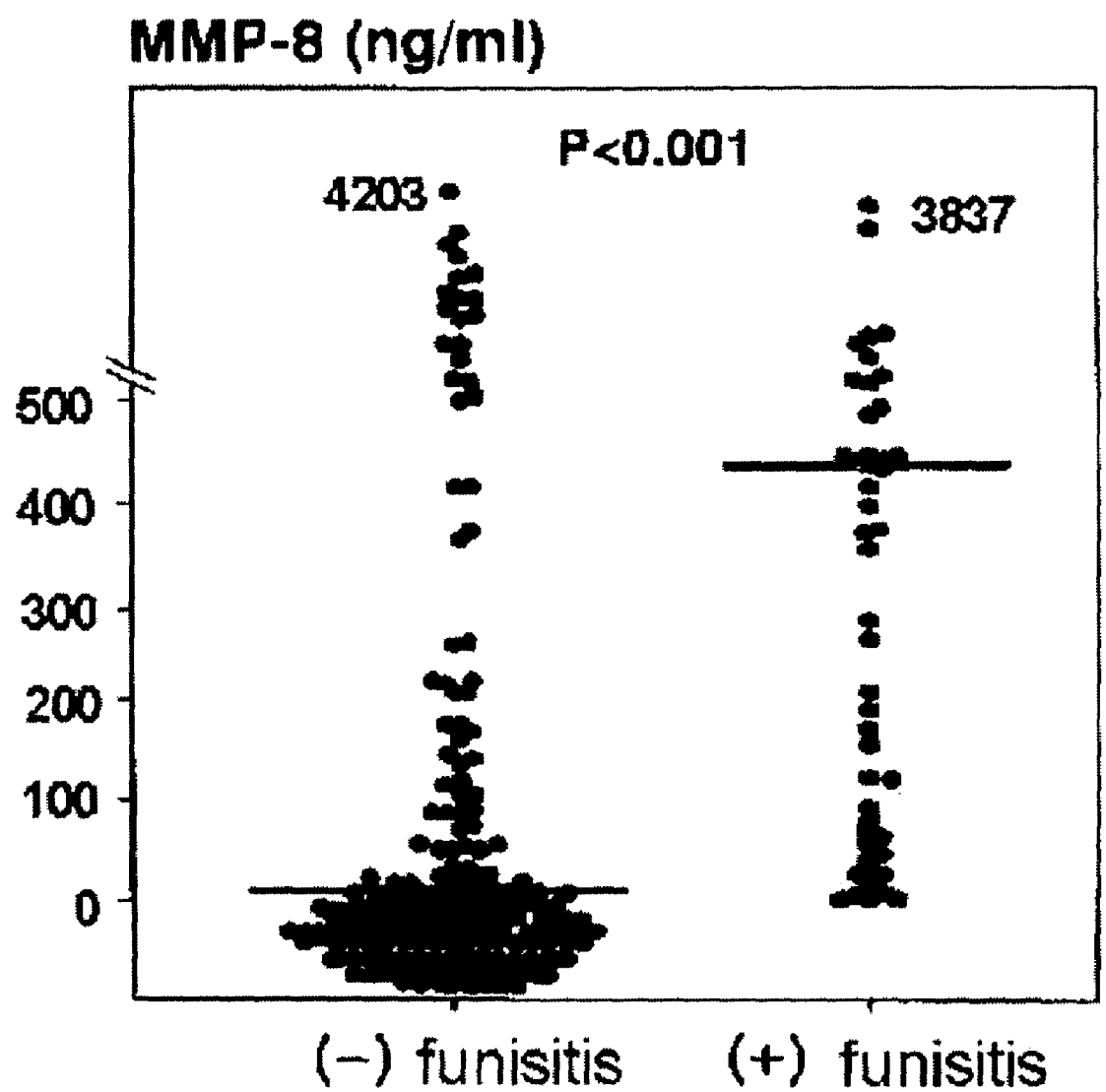
FIG. 3 shows distributions of amniotic fluid MMP-8 concentrations in patients with and without funisitis.

The fetal inflammatory response syndrome (FIRS) is a multi-system disorder associated with impending preterm delivery and adverse neonatal outcome. Regarded as the histologic counterpart of FIRS, inflammation of the umbilical cord (funisitis) has been associated with an increased risk for the development of cerebral palsy. Neutrophils found in the amniotic cavity are of fetal origin. Based on these findings, it is hypothesized that secretory products from neutrophils might be an index of FIRS. To test this hypothesis, the relationship between amniotic fluid matrix metalloproteinase-8 (MMP-8) and funisitis was examined. The MMP-8 concentration was observed to be significantly higher in the presence of funisitis than in the absence of funisitis. The diagnostic indices of MMP-8 in the identification of funisitis were found to be high in sensitivity, specificity, and negative predictive value (see Tables 5 and 6, and FIGS. 3 and 4).

From these results, it was found that there is a strong association between amniotic fluid MMP-8 concentrations and fetal inflammation (funisitis). Therefore, the present invention proposes that assessment of amniotic fluid MMP-8 concentrations may assist the diagnosis of the fetal infection without resorting to conventional invasive fetal blood sampling.

With the evidence of the correlation between the amniotic fluid MMP-8 concentration and fetal infection, the present inventors studied the relationship between amniotic fluid MMP-8 concentrations and neonatal morbidity, which includes neonatal sepsis, respiratory distress syndrome, pneumonia, bronchopulmonary dysplasia, necrotizing enterocolitis, and intraventricular hemorrhage. A significantly higher MMP-8 concentration was seen in the presence of neonatal morbidity than in the absence of neonatal morbidity (see Table 7). The diagnostic indices of MMP-8 in the identification of neonatal morbidity were excellent in specificity, and positive and negative predictive values (see Table 7 and 8). Additionally, the amniotic fluid MMP-8 concentration was significantly higher in patients who delivered neonates with neonatal sepsis than in those who delivered neonates without neonatal sepsis (P<0.05) (see Table 9).

The data, taken together, demonstrates that amniotic fluid MMP-8 concentration can be useful as a diagnostic marker in the prediction of neonatal sepsis and perinatal morbidity.

Intrauterine infection or inflammation has been implicated in the etiology of cerebral palsy. FIRS is believed to cause fetal brain damage in term and preterm birth. Neutrophils are the cells most frequently recruited into the amniotic fluid in cases of infection and they are considered to be of fetal origin. The amniotic fluid level of MMP-8, an enzyme secreted by activated neutrophils, was found to be significantly higher in cases of intrauterine infection and/or inflammation, as demonstrated in the following Examples 2 and 3. Based on this background, an examination was made to determine if increased concentrations of matrix metalloproteinase-8 (MMP-8) in amniotic fluid are associated with the development of cerebral palsy at the age of three.

Figure 5:
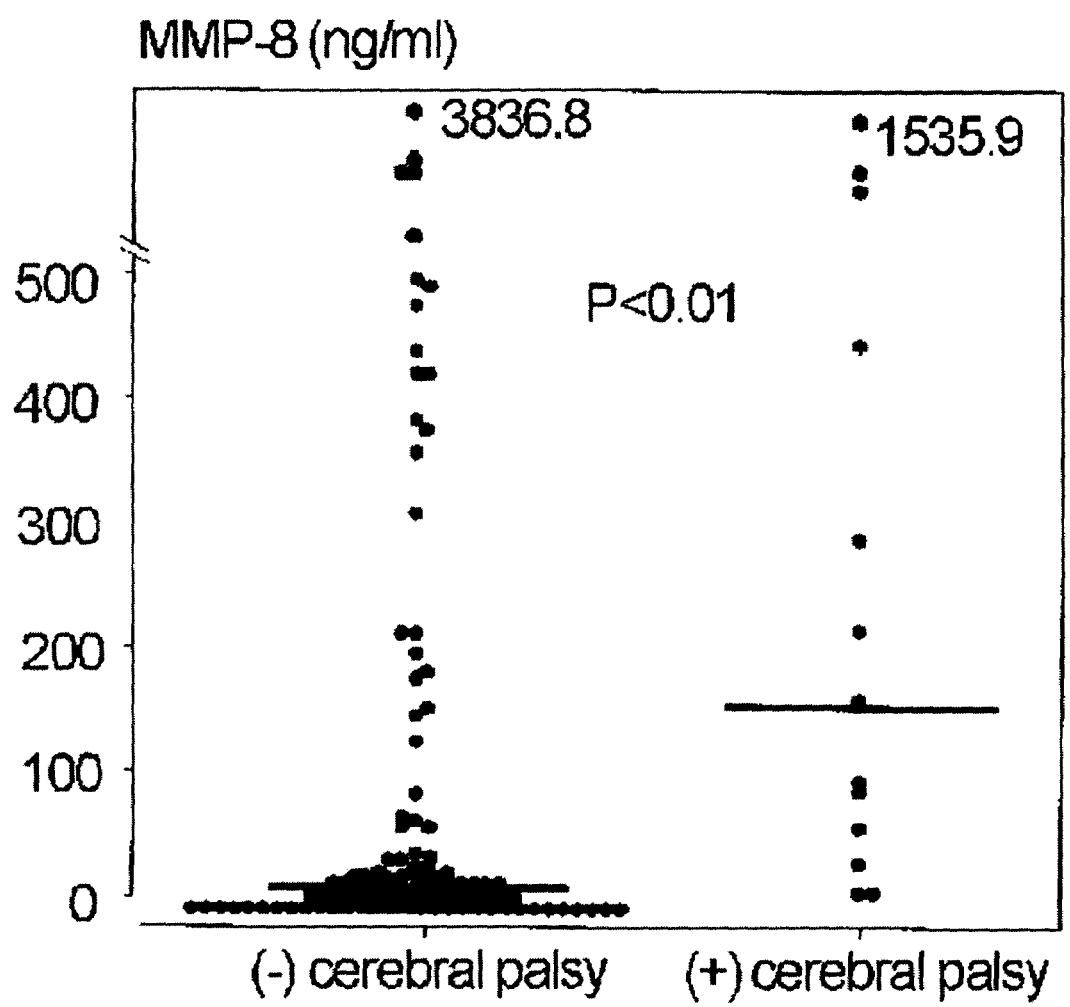
FIG. 5 shows distributions of amniotic fluid MMP-8 concentrations in patients with and without prenatal development of cerebral palsy.
Figure 6:
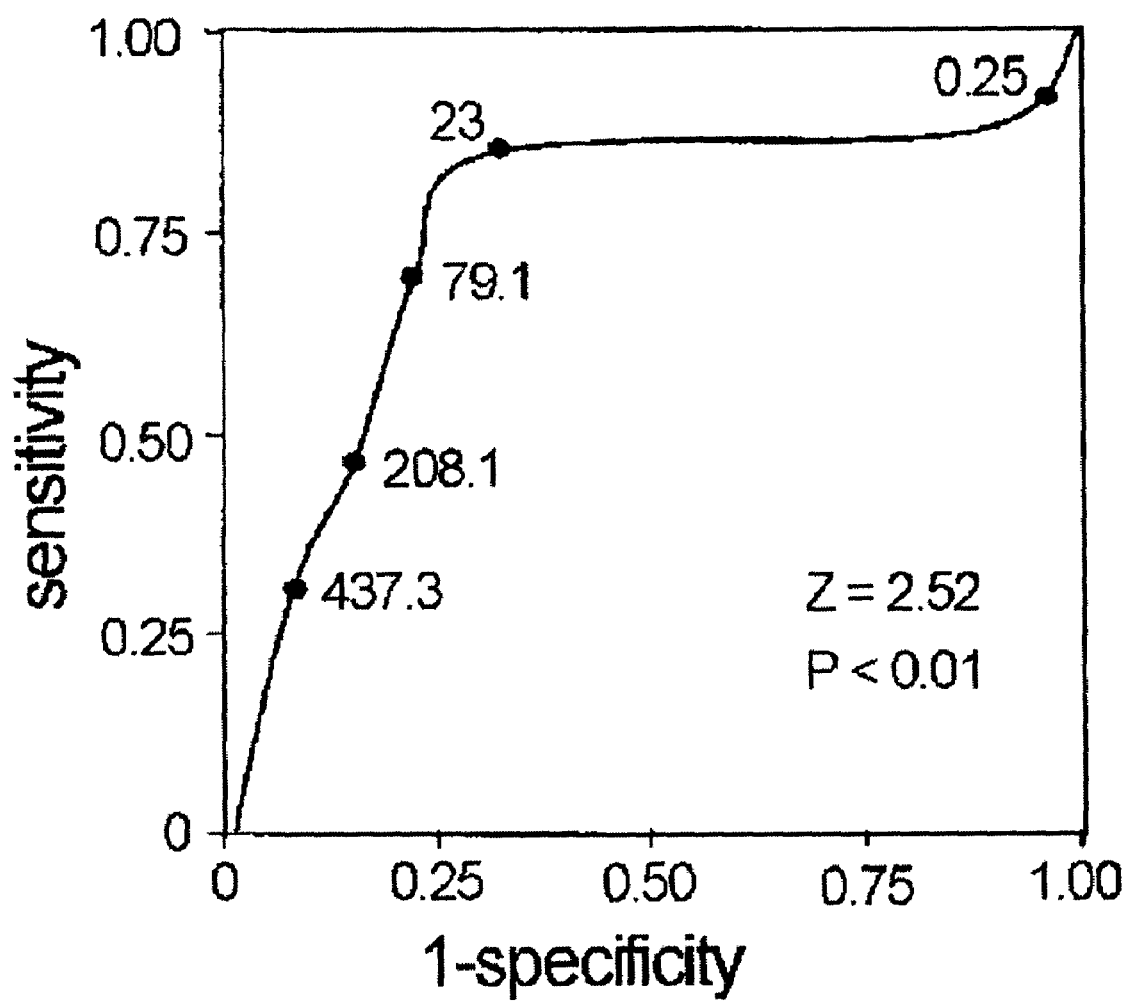
FIG. 6 shows a receiver operating characteristic curve in which sensitivity versus specificity is plotted to select a cutoff value for MMP-8 in the identification of prenatal development of cerebral palsy.

A significantly higher level of MMP-8 was observed in the amniotic fluid taken from the patients whose newborns developed cerebral palsy, compared to those whose newborns did not develop cerebral palsy (see FIG. 5), demonstrating that MMP-8 is very useful as a diagnostic marker for the prediction of cerebral palsy (see FIGS. 5 and 6, and Table 11).

We could see that the elevated amniotic fluid MMP-8 concentration is associated with odds that are six-fold higher of developing cerebral palsy. That is, the amniotic fluid MMP-8 concentration can be used as a prenatal diagnostic marker for the prediction of cerebral palsy.

After extensive studies, a cutoff value of amniotic fluid MMP-8 in the identification of preterm delivery, fetal infection, and fetal damage was selected. In this regard, the pregnant woman is identified as being at risk for preterm delivery, neonatal morbidity, fetal infection (funisitis), and cerebral palsy when the cutoff value of amniotic fluid MMP-8 is higher than 5-100 ng/ml and preferably higher than 10-50 ng/ml.

Based on the usefulness of the amniotic fluid MMP-8 concentration as a diagnostic marker in the identification of preterm delivery, fetal infection, and fetal damage, a reagent system can be developed for diagnosing preterm delivery, fetal infection, and fetal damage.

Therefore, in another embodiment of the present invention, a diagnostic reagent system for the identification of preterm delivery, fetal infection, and fetal damage, which is based on the quantification of amniotic fluid MMP-8 concentrations, is provided. In detail, the diagnostic reagent system makes use of an analytic mechanism comprising the steps of:

1) adsorbing primary MMP-8 antibodies onto a matrix; and 2) incubating the MMP-8 antibodies adsorbed onto the matrix in the presence of an amniotic fluid and washing the matrix to remove unbound antigens;

3) coupling a secondary chromogenic enzyme- or fluorescent-linked antibody to the MMP-8 bound to the primary antibodies adsorbed onto the matrix; and 4) developing a chromogenic reaction in the matrix by use of a coloring agent with quantitative analysis of the amount of antibody-bound MMP-8.

Examples of the matrix useful in step 1 include a nitrocellulose membrane, a 96-well plate of polyvinyl resin, a 96-well plate of polystyrene resin, and a glass slide.

For quantitative analysis, the secondary antibody to be coupled to the MMP-8 bound to the primary antibody is linked to a chromogenic enzyme, such as peroxidase, alkaline phosphatase, and biotin, or a fluorescent agent such as FITC (Fluorescein Isothiocyanate) and TRITC.

The coloring agent can be selected from a group of agents consisting of 4CN (4-chloro-1-naphthol), DAB (diaminobenzidine), AEC (aminoethyl carbazol), ABTS (2,2'-azino-bis(3-ethylbenzothiazoline-6-sulfonic acid)), OPD (O-phenylenediamine) and TMB (tetramethyl benzidine).

In principle, the diagnosis is based on the quantification of amniotic fluid MMP-8 concentrations, which takes advantage of the reaction of MMP-8 to its antibodies. In this connection, monoclonal or polyclonal anti-MMP-8 antibodies are immobilized to a solid matrix and reacted to MMP-8 in a sample, followed by washing the matrix to remove unbound antibodies and MMP-8. Then, a secondary monoclonal or polyclonal antibody which is linked with an enzyme or a fluorescent is bound to the immobilized MMP-8. A horseradish peroxidase polyclonal antibody or a biotinylated rabbit polyclonal or monoclonal antibody is usually used as the secondary antibody. A chromogenic reaction for visualization is developed in the presence of a peroxide and a coloring agent. Addition of an acid halts the chromogenic reaction, followed by the measurement of absorbance at 450 nm.

Based on this diagnostic mechanism, a diagnostic kit can be configured, which uses the same diagnostic reagent system.

Therefore, in a further embodiment of the present invention, a diagnostic kit for the identification and prediction of preterm delivery, fetal infection, and fetal damage is provided. With the aid of the diagnostic kit, preterm labor or premature rupture of fetal membranes can be assessed quantitatively or qualitatively with convenience. For the assay of an MMP-8 antigen, a marker antibody is prepared by coupling gold or colloid particles to an anti-MMP-8 antibody. The marker antibody against MMP-8 is bound to MMP-8 to form an immune complex. This immune complex is again reacted with the MMP-8 antibody, and then washing fluid for excess marker antibody, usually made of urea etc., is added. A positive result can be visualized by the eye when the MMP-8 concentration exceeds a certain level. Such a diagnostic kit may comprise anti-MMP-8 antibody, standard MMP-8, matrix, assay buffer, chromogenic enzyme- or fluorescent-labeled secondary antibody, and adhesive plate cover.

Alternatively, the diagnostic kit of the present invention may adopt an automated analytic method using a biological microchip. For instance, a diagnostic kit can be structured to perform immunoblotting using an anti-MMP-8 antibody-coated slide glass. This diagnostic kit may comprise a biological microchip with an anti-MMP-8 antibody immobilized onto its surface, appropriate buffer, standard MMP-8, and secondary antibody.

EXAMPLES

A better understanding of the present invention may be obtained in light of the following examples which are set forth to illustrate, but are not to be construed to limit the present invention.

Example 1

Selection of Diagnostic Cutoff Value for Prenatal Diagnosis of Preterm Delivery Strong evidence implicates chronic intrauterine infection in the etiology of preterm delivery. In this example, an examination was conducted to determine if amniotic fluid concentrations of MMP-8 and interleukin-6 (IL-6) can be used to identify patients at risk for spontaneous preterm delivery among pregnant women without clinical signs of preterm delivery.

To this end, a case-control study was designed with stored amniotic fluid obtained from women who had mid-trimester genetic amniocentesis. Amniotic fluid levels of MMP-8 and IL-6 were determined by ELISA in 19 patients with a spontaneous preterm delivery before 32 weeks of gestation, and 95 patients who delivered normal neonates at full-term as control cases. Cases with an abnormal fetal karyotype and major anomalies were excluded from this analysis.

The median amniotic fluid MMP-8 concentration with spontaneous preterm delivery was 3.1 [0.3-1954.9] ng/ml, while the level was 1.3 [<0.3-45.2] ng/ml in the control cases. The median amniotic fluid IL-6 concentration was 0.32 [0.04-2.52] ng/ml in patients with spontaneous preterm delivery while the level was 0.18 [0.01-1.81] ng/ml in the control cases. Both MMP-8 and IL-6 concentrations of amniotic fluid taken at mid-pregnancy stage were significantly higher in patients with spontaneous preterm delivery than in the control cases with full-term delivery ($p<0.01$), as shown in FIG. 1.

After the assessment of MMP-8 concentrations in patients and the control cases, when the amniotic fluid MMP-8 concentration at a mid-pregnancy stage was above 23 ng/ml, 89% of the cases investigated had a spontaneous preterm delivery.

Figure 2:
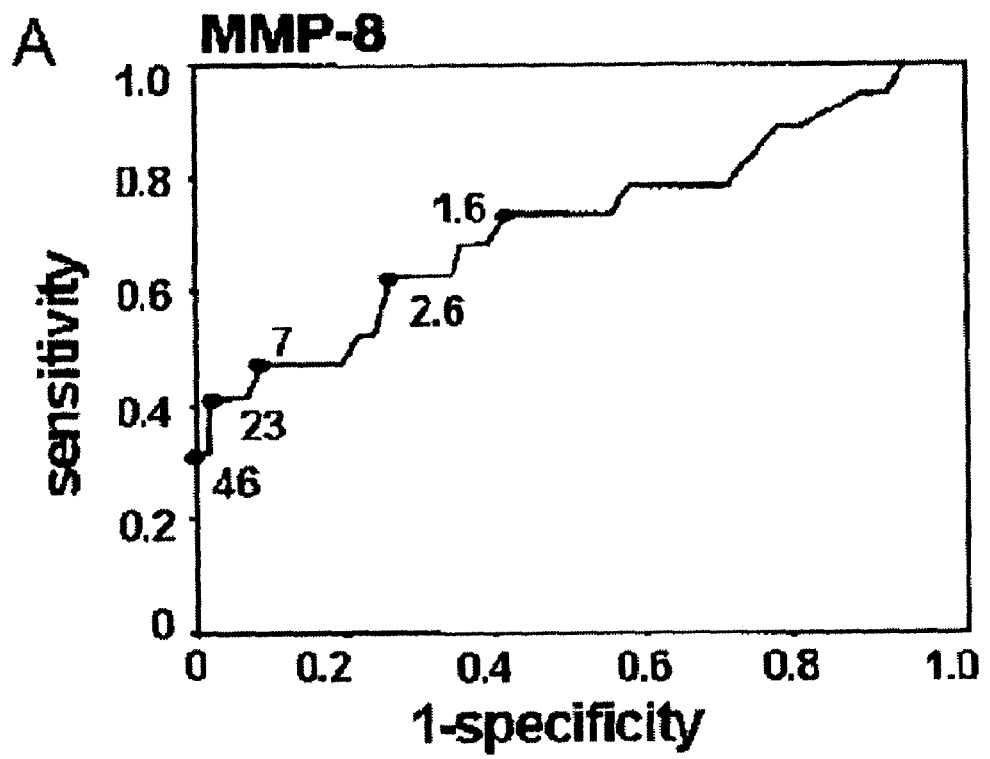
FIG. 2 shows receiver operating characteristic curves in which sensitivity versus specificity is plotted to select a cutoff value for amniotic fluid MMP-8 in the identification of spontaneous preterm delivery.
Figure 2:
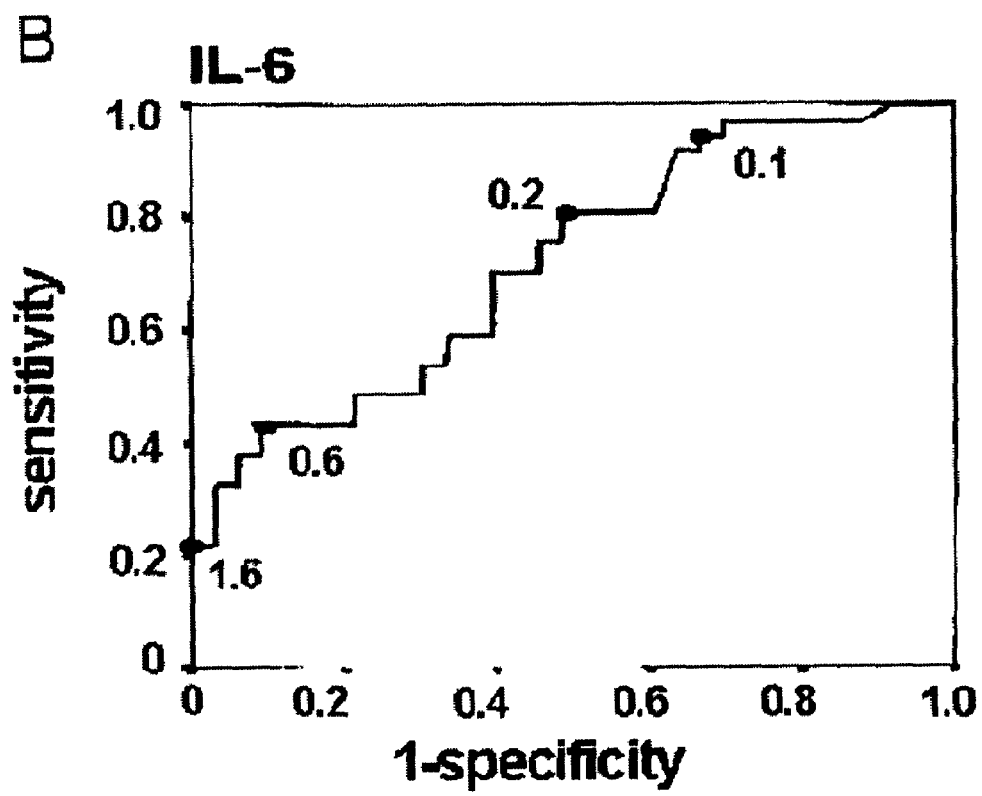

Additionally, an amniotic fluid MMP-8 cutoff value of 23 ng/ml at a mid-pregnancy stage showed a sensitivity of 42% (8/19) and a specificity of 99% (94/95) in the identification of the patients with early preterm delivery after genetic amniocentesis, while an IL-6 cutoff value of 0.6 ng/ml showed a sensitivity of 42% (8/19) and a specificity of 92% (87/95), as shown in FIG. 2. MMP-8 was therefore superior to IL-6 in sensitivity, specificity and odds ratio for the identification and prediction of preterm delivery. Consequently, an amniotic fluid MMP-8 concentration of 23 ng/ml was selected as a cutoff value in the identification of prematurity.

Example 2

Relationship Between Amniotic Fluid Concentration of MMP-8 and Intrauterine Infection and Inflammation Amniotic fluid concentrations of MMP-8 were examined in the presence or absence of intrauterine infection and inflammation to determine if the amniotic fluid MMP-8 concentration could be used as a diagnostic marker in the identification of intrauterine infection and fetal damage.

In this regard, 255 consecutive patients who delivered preterm singleton neonates (gestational age <36 weeks) within 72 hours of amniocentesis at Seoul National University Hospital in Seoul, Korea were examined. The amniotic fluids were measured for their MMP-8 levels as well as cultured for aerobic and anaerobic bacteria and mycoplasmas. In addition, histologic examination of the placenta was performed. Amniotic fluid was retrieved by transabdominal amniocentesis under ultrasonographic guidance.

2-1: Amniotic Fluid Culture

Immediately after being retrieved by transabdominal amniocentesis, the amniotic fluid was put into sterile plastic vessels with caps and stored therein until culturing in anaerobic or aerobic media. Useful in culturing aerobes or anaerobes were blood agar, McConkey's agar, Bactec 6A vial, thioglycollate broth, brucellar blood agar, fresh meat extracts, and pleuropneumoni-like organism broth supplemented with horse serum penicillin polymixin B and amphotericin B. Mycotrim GU was used to culture mycoplasmas.

2-2: Measurement of Amniotic Fluid MMP-8 Concentration

Amniotic fluid samples were centrifuged at 700×g for 10 min. The supernatant was used to measure the amniotic fluid MMP-8 concentration with ELISA (Amersham Pharmacia Biotech, UK) using two monoclonal antibodies which bind to non-overlapping epitopes.

2-3: Histologic Examination of Placenta

After the placenta was fully drawn out at delivery, tissues excised from the umbilical cord, the chorionic plate, and the placental membrane were fixed in 10% formalin and embedded in paraffin to prepare slides. Afterwards, the tissue segments were dyed with hematoxylin and eosin for visualization under a microscope. Acute intrauterine inflammation was defined as the presence of inflammatory changes on examination of any of the fetal membrane, chorionic membrane, decidua and the chorionic plate.

Of the 255 subjects, 45 cases were found to have positive amniotic fluid culture, which shows the intrauterine infection frequency to be 18%. On histologic examination of the placenta 113 patients were found to have chorioamnionitis, which indicates the intrauterine inflammation frequency to be 44%. The median amniotic fluid MMP-8 concentration was detected at a level of 191.4 ng/ml in patients with a positive amniotic fluid culture of bacteria and at a level of 2.7 ng/ml in those with a negative culture. Therefore, the median amniotic fluid MMP-8 concentration in patients with intrauterine infection was significantly higher than those without intrauterine infection ($p<0.001$). The results are given in Table 1, below.

TABLE 1

Amniotic Fluid MMP-8 Concentration According to Amniotic Fluid Culture Result

| Bacteria in Amniotic Fluid | Median Value (ng/mL) | Interval (ng/mL) |
|---|---|---|
| Positive | 191.4 | <0.3–4202.7 |
| Negative | 2.7 | <0.3–3929.0 |

With a cutoff value of 23 ng/ml, the diagnostic indices of MMP-8 for the identification of positive amniotic fluid cultures were excellent: sensitivity of 76% and negative predictive value of 93%. The results are given in Table 2, below.

TABLE 2

Diagnostic Indices of MMP-8 for the Identification of Positive Amniotic Fluid Culture

| | |
|---|---|
| Sensitivity | 76% |
| Specificity | 70% |
| Positive Predictive Value | 35% |
| Negative Predictive Value | 93% |

Histologic examination of the placenta revealed that the median concentration of amniotic fluid MMP-8 was 160.9 ng/ml in the presence of chorioamnionitis, but 1.0 ng/ml in the absence of chorioamnionitis. The amniotic fluid MMP-8 concentration was significantly higher in patients with chorioamnionitis than those without chorioamnionitis ($p<0.001$). The results are given in Table 3, below.

TABLE 3

MMP-8 Concentration According to Intrauterine Inflammation

| Histologic Chorioamnionitis | Median Value (ng/mL) | Interval (ng/mL) |
|---|---|---|
| Present | 160.9 | <0.3–4202.7 |
| Absent | 1.0 | <0.3–766.2 |

With a cutoff value of 23 ng/ml, the diagnostic indices of MMP-8 for the identification of intrauterine inflammation (chorioamnionitis) were excellent: sensitivity of 72%, specificity of 89%, positive predictive value of 84%, and negative predictive value of 80%. The results are given in Table 4, below.

TABLE 4

Diagnostic Indices for the Identification of Intrauterine Inflammation

| | |
|---|---|
| Sensitivity | 72% |
| Specificity | 89% |
| Positive Predictive Value | 84% |
| Negative Predictive Value | 80% |

Example 3

Diagnosis of Funisitis by Use of Amniotic Fluid Concentration of MMP-8

Amniotic fluid MMP-8 concentrations were measured in the presence or in the absence of funisitis to determine if amniotic fluid MMP-8 concentrations could be utilized to directly diagnose fetal infection.

The relationship between the presence of funisitis and amniotic fluid concentrations of MMP-8 was examined in 255 consecutive patients who delivered preterm singleton neonates (gestational age <36 weeks) within 72 hours of amniocentesis at the Seoul National University Hospital in Seoul, Korea. Funisitis was diagnosed by the presence of neutrophil infiltration into the umbilical vessel walls or Wharton jelly. Quantification of MMP-8 concentration was conducted in the same manner as in Example 2.

Funisitis was diagnosed in 59 cases (funisitis frequency 23%). The median amniotic fluid MMP-8 concentration was 433.7 ng/ml in patients with funisitis and 1.9 ng/ml in those without funisitis. Therefore, the patients with funisitis had a significantly higher median amniotic fluid MMP-8 concentration compared to those without funisitis ($p<0.001$). The results are given in Table 5, below and FIG. 3.

TABLE 5

MMP-8 Concentration According to Presence or Absence of Funisitis

| Funisitis | Median Value (ng/mL) | Interval (ng/mL) |
|---|---|---|
| Present | 433.7 | 1.5–3836.8 |
| Absent | 1.9 | <0.3–4202.7 |

Figure 4:
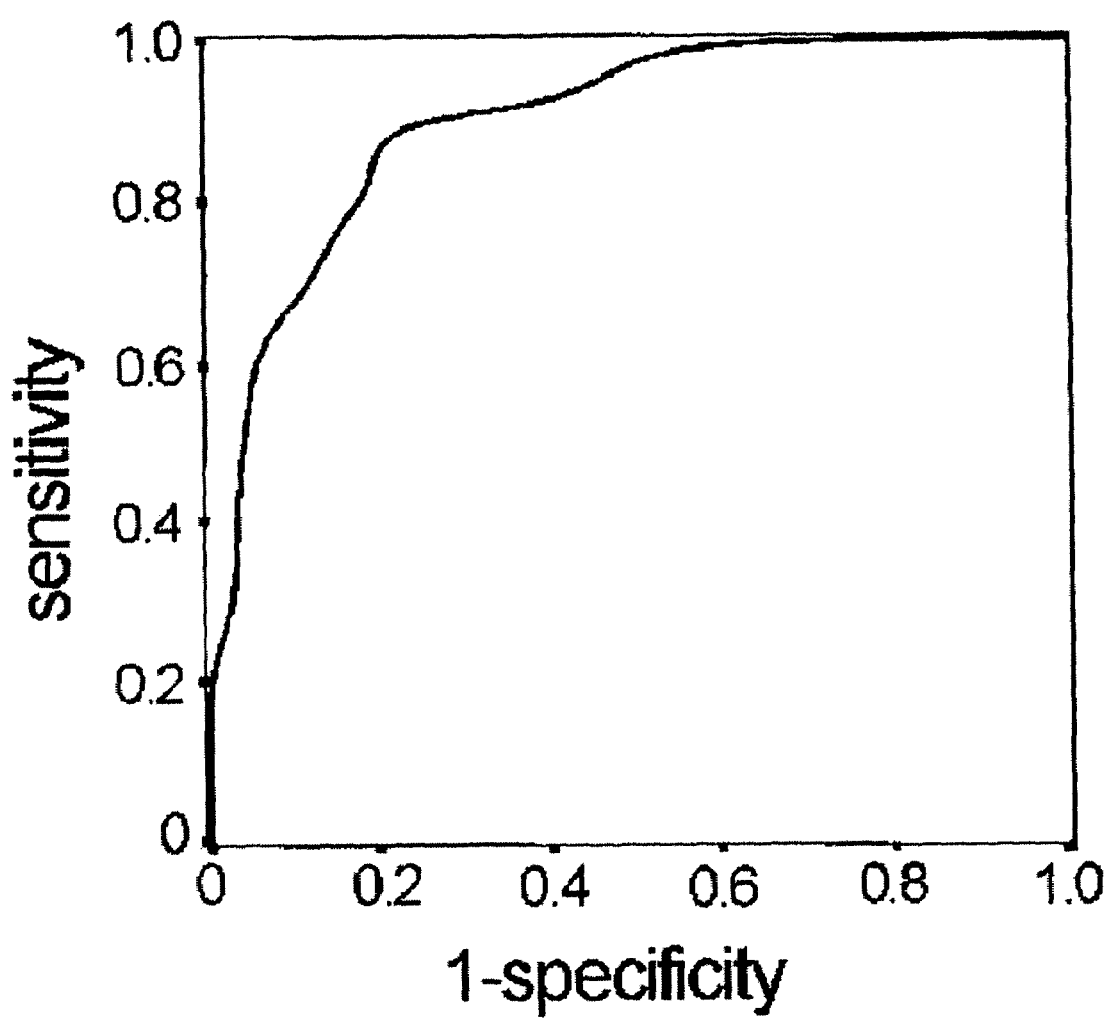
FIG. 4 shows a receiver operating characteristic curve in which sensitivity versus specificity is plotted to select a cutoff value for MMP-8 in the identification of funisitis.

Receiver operating characteristic curve analysis was employed to select a cutoff value for amniotic fluid analytes in the diagnosis of funisitis. As a result, a cutoff of 23 ng/ml was selected for MMP-8 in consideration of both sensitivity and positive predictive value for the diagnosis of funisitis, as seen in FIG. 4. The diagnostic indices of MMP-8 (cutoff 23 ng/ml) in the identification of funisitis were excellent: sensitivity of 90%, specificity of 78%, and negative predictive value of 96%. The results are summarized in Table 6, below.

TABLE 6

Diagnostic Indices of MMP-8 for the Identification of Funisitis

| | |
|---|---|
| Sensitivity | 90% (53/59) |
| Specificity | 78% (153/196) |
| Positive Predictive Value | 55% (53/96) |
| Negative Predictive Value | 96% (153/159) |

Example 4

Diagnosis of Neonatal Morbidity by Use of Amniotic Fluid MMP-8 Concentration

Based on the postulation that funisitis is associated with an increased risk of neonatal infection-related complications such as sepsis, pneumonia, bronchopulmonary dysplasia, necrotizing enterocolitis, and intraventricular hemorrhage, amniotic fluid MMP-8 concentrations in cases with such neonatal morbidity were compared with those in normal cases.

The relationship between the presence of such neonatal morbidity and amniotic fluid concentration of MMP-8 was examined in 239 consecutive patients who delivered preterm singleton neonates (gestational age <36 weeks) within 72 hours of amniocentesis at the Seoul National University Hospital in Seoul, Korea. Neonatal morbidity was defined by the development of neonatal complications, such as sepsis, pneumonia, bronchopulmonary dysplasia, necrotizing enterocolitis, and intraventricular hemorrhage. Congenital neonatal sepsis was diagnosed in the presence of a positive blood culture within 72 hours of delivery. The diagnosis of neonatal respiratory distress syndrome required the presence of respiratory grunting and retracting, an increased oxygen requirement ($FiO_2>0.4$), and diagnostic radiographic and laboratory findings without the evidence of other causes of respiratory disease. Pneumonia was diagnosed in the presence of definite clinical and radiologic findings, with or without a positive culture from tracheal aspirate or chest tube specimen within 7 days of birth. Bronchopulmonary dysplasia was diagnosed by the criteria proposed by Bancalari et al.: (1) Intermittent positive-pressure ventilation was required during the first week of life and for a minimum of 3 days; (2) clinical signs of chronic respiratory disease developed, characterized by tachypnea, intercostal and subcostal retraction, and rales on auscultation, all persisting for longer than 28 days; (3) supplemental oxygen was required for more than 28 days to maintain a $PaO_2$ over 50 mmHg; (4) chest radiograph showed persistent strands of densities in both lungs, alternating with areas of normal or increased lucency. In some cases, an autopsy was needed for the diagnosis of bronchopulmonary dysplasia. Intraventricular hemorrhage was graded according to the system proposed by McMenamin et al. Necrotizing enterocolitis was diagnosed in the presence of abdominal expansion and feeding intolerance for at least 24 hours with radiologic findings of air entrapment in enteric walls, intestinal rupture, and meconium obstructive syndrome, or by operational or autopsic findings of necrotic intestinal rupture. Quantification of amniotic fluid MMP-8 concentrations was conducted in the same manner as in Example 2.

107 neonates of the 239 subjects (frequency 45%) were diagnosed as suffering from neonatal morbidity. The median amniotic fluid MMP-8 concentration remained at a level of 2.35 ng/ml in the absence of major neonatal morbidity while a significantly higher MMP-8 concentration (160.9 ng/ml) was observed in the presence of major neonatal morbidity (p<0.001). Details are given in Table 7, below.

TABLE 7

MMP-8 Concentration According to the Presence or Absence of Neonatal Morbidity

| Neonatal Morbidity | Median Value (ng/mL) | Interval (ng/mL) |
|---|---|---|
| Present | 17.0 | <0.3–4202.7 |
| Absent | 2.35 | <0.3–1333.1 |

Receiver operating characteristic curve analysis was employed to select a cutoff value for amniotic fluid analytes in the diagnosis of neonatal morbidity. As a result, a cutoff of 23 ng/ml was selected for MMP-8 considering sensitivity and positive predictive value for the diagnosis of neonatal morbidity. The diagnostic indices of MMP-8 (cutoff 23 ng/ml) for the identification of neonatal morbidity were excellent: specificity of 77%, positive predictive value of 63% and negative predictive value of 65%. The results are summarized in Table 8, below.

TABLE 8

Diagnostic Indices of MMP-8 for the Identification of Neonatal Morbidity

| Sensitivity | 50% |
|---|---|
| Specificity | 77% |
| Positive Predictive Value | 63% |
| Negative Predictive Value | 65% |

Additionally, the median amniotic fluid MMP-8 concentration was significantly higher in the presence of sepsis (208.95 ng/ml), compared to the absence of sepsis (4.4 ng/ml) (p<0.05). Details are given in Table 9, below.

TABLE 9

MMP-8 Concentration According to the Presence or Absence of Neonatal Sepsis

| Neonatal Sepsis | Median Value (ng/mL) | Interval (ng/mL) |
|---|---|---|
| Present | 208.95 | 2.4–1568.6 |
| Absent | 4.4 | <0.3–4202.7 |

The diagnostic indices of MMP-8 (cutoff 23 ng/ml) in the identification of neonatal sepsis were excellent: sensitivity of 67%, specificity of 66%, and negative predictive value of 99%. The results are summarized in Table 10, below.

TABLE 10

Diagnostic Indices of MMP-8 for the Identification of Neonatal Sepsis

| Sensitivity | 67% |
|---|---|
| Specificity | 66% |
| Positive Predictive Value | 5% |
| Negative Predictive Value | 99% |

Example 5

Diagnosis of Cerebral Palsy by Use of Amniotic Fluid MMP-8 Concentration

The relationship between amniotic fluid concentrations of MMP-8 and the development of cerebral palsy was examined in 116 preterm singleton newborns (gestational age at birth, <35 weeks) born to mothers who underwent amniocentesis and were followed for at least three years. Cerebral palsy was diagnosed in the presence of a definite abnormality on the neurodevelopmental assessment (abnormality of developmental milestone, postural abnormality by the Vojta method, and reflex abnormality) and a persistent abnormality of muscle tone.

Median amniotic fluid concentration of MMP-8 was significantly higher in mothers whose newborns developed cerebral palsy than in mothers whose newborns did not develop cerebral palsy (median 153.9 [range <0.3-1535.9] ng/ml versus median 6.4 [range <0.3-3836.8] ng/ml; p<0.01). Neonates who developed cerebral palsy were delivered at earlier gestational age than those without cerebral palsy. After adjustment for the gestational age at birth and the results of amniotic fluid culture, elevated concentrations of amniotic fluid MMP-8 significantly increased the odds of development of cerebral palsy (odds ratio, 6.0; 95% confidence interval, 1.1-33.0; p<0.05).

Receiver operating characteristic curve analysis was employed to select a cutoff value for amniotic fluid analytes in the diagnosis of cerebral palsy. As a result, a cutoff of 23 ng/ml was selected for MMP-8 in consideration of both sensitivity and positive predictive value for the diagnosis of cerebral palsy, as shown in FIG. 6. The diagnostic indices of MMP-8 (cutoff 23 ng/ml) in the diagnosis of cerebral palsy were excellent: sensitivity of 85%, specificity of 69%, and negative predictive value of 97%. The results are summarized in Table 11, below.

TABLE 11

Diagnostic Indices of MMP-8 for Cerebral Palsy

| Sensitivity | 85% |
|---|---|
| Specificity | 69% |
| Positive Predictive Value | 26% |
| Negative Predictive Value | 97% |

INDUSTRIAL APPLICABILITY

As described hereinbefore, a diagnostic reagent system and a diagnostic kit are provided for the prenatal diagnosis of preterm delivery, fetal infection, and fetal damage, based on the quantification of amniotic fluid MMP-8 concentration. Taking advantage of an antigen-antibody reaction coupled with chromogenesis, the diagnostic reagent system and diagnostic kit of the present invention is characterized by comprising one or more anti-MMP-8 antibody. The diagnostic reagent system and kit of the present invention can be applied to patients with or without clinical signs of preterm delivery or premature rupture of fetal membranes. Superior in sensitivity and specificity to conventional methods of measuring fetal blood cytokine levels, the present invention is very useful in prenatal diagnosis of preterm delivery, fetal infection, and fetal damage.

What is claimed is:

1. A diagnostic method for prenatal identification of an increased risk of preterm delivery of a pregnant woman without clinical symptoms of preterm labor or preterm premature rupture of membrane at midtrimester, comprising the steps of:
   1) sampling amniotic fluid from the pregnant woman at midtrimester; and
   2) measuring matrix metalloproteinase-8 level in the amniotic fluid sample by an immunoassay, and determining that the matrix metalloproteinase-8 level is greater than about 23 ng/ml in the amniotic fluid as an indication that the pregnant woman is at increased risk for preterm delivery.

2. The method according to claim 1, wherein step 2) comprises the steps of:
   1) adsorbing primary anti-matrix metalloproteinase-8 antibodies onto a matrix,
   2) incubating the primary anti-matrix metalloproteinase-8 antibodies adsorbed onto the matrix with the amniotic fluid sample,
   3) coupling chromogenic enzyme- or fluorescent agent-linked secondary anti-matrix metalloproteinase-8 antibodies to the matrix metalloproteinase-8 that is bound to the primary antibodies adsorbed onto the matrix,
   4) developing a chromogenic reaction with a coloring agent and measuring absorbance of the chromogenic reaction when the chromogenic enzyme-linked antibodies are used, or
   measuring fluorescence when the fluorescent agent-linked antibodies are used in the matrix as an indication of the matrix metalloproteinase-8 level in the amniotic fluid sample; and
   5) determining whether matrix metalloproteinase-8 level is greater than about 23 ng/ml.

3. The method according to claim 2, wherein the anti-matrix metalloproteinase-8 primary and secondary antibodies are independently monoclonal or polyclonal.

4. The method according to claim 3, wherein the primary and secondary antibodies are monoclonal.

5. The method according to claim 2, wherein the matrix is selected from the group consisting of a nitrocellulose membrane, a 96-well plate of polyvinyl resin, a 96-well plate of polystyrene resin, and a glass slide.

6. The method according to claim 2, wherein the chromogenic enzyme is selected from the group consisting of peroxidase and alkaline phosphatase.

7. The method according to claim 2, wherein the fluorescent agent is selected from the group consisting of FITC and TRITC.

8. The method according to claim 2, wherein the coloring agent is selected from the group consisting of 4-chloro-1-naphtol, diaminobenzidine, aminoethyl carbazole, 2,2'-azion-bis(3-ethylbenzothiazoline-6-sulfonic acid), o-phenylenediamine, and tetramethyl benzidine.

* * * * *